(12) United States Patent
Kelley

(10) Patent No.: US 8,426,464 B2
(45) Date of Patent: Apr. 23, 2013

(54) LIQUID PEST CONTROL FORMULATION

(75) Inventor: Donald W Kelley, Athens, TX (US)

(73) Assignee: Sergeant's Pet Care Products, Inc., Omaha, NE (US)

( * ) Notice: Subject to any disclaimer, the term of this patent is extended or adjusted under 35 U.S.C. 154(b) by 0 days.

(21) Appl. No.: 13/275,725

(22) Filed: Oct. 18, 2011

(65) Prior Publication Data

US 2012/0035223 A1   Feb. 9, 2012

Related U.S. Application Data

(62) Division of application No. 12/876,122, filed on Sep. 4, 2010, now Pat. No. 8,367, 088.

(60) Provisional application No. 61/249,968, filed on Oct. 8, 2009.

(51) Int. Cl.
   *A01N 25/02* (2006.01)
   *A01N 25/32* (2006.01)
   *A01N 37/34* (2006.01)
   *A61K 31/275* (2006.01)

(52) U.S. Cl.
   USPC .......................................... 514/520; 424/405

(58) Field of Classification Search ............ 514/520
   See application file for complete search history.

(56) References Cited

U.S. PATENT DOCUMENTS

| | | | |
|---|---|---|---|
| 4,160,335 A | 7/1979 | Von Kohorn et al. | |
| 4,451,482 A * | 5/1984 | Cagen | 514/458 |
| 4,607,050 A | 8/1986 | Kieran et al. | |
| 4,639,393 A | 1/1987 | Von Kohorn et al. | |
| 4,737,520 A | 4/1988 | Naik et al. | |
| 5,437,869 A | 8/1995 | Kelley | |
| 5,492,696 A | 2/1996 | Price et al. | |
| 5,589,181 A | 12/1996 | Bencsits | |
| 5,602,107 A | 2/1997 | Choi | |
| 5,942,525 A | 8/1999 | Pennington et al. | |
| 6,001,382 A | 12/1999 | Levy | |
| 6,068,848 A * | 5/2000 | Gubernick et al. | 424/401 |
| 6,569,809 B1 | 5/2003 | Sato et al. | |
| 2003/0091603 A1 | 5/2003 | Ohmori et al. | |
| 2004/0192650 A1 | 9/2004 | Kelley | |
| 2006/0252728 A1 | 11/2006 | Sirinyan et al. | |
| 2006/0264402 A1 | 11/2006 | Kelley | |
| 2008/0118585 A1 | 5/2008 | Nouvel | |
| 2008/0293809 A1 | 11/2008 | Kelley | |
| 2010/0016398 A1 * | 1/2010 | Sirinyan et al. | 514/407 |

FOREIGN PATENT DOCUMENTS

WO   WO 2008/080542   *   7/2008

OTHER PUBLICATIONS

Miyamoto et al. "Pyrethroids, nerve poisons: how their risks to human health should be assessed" Toxicology Letters, 1995, 82/83, 933-940.*
Opinion on Diethylene Glycol Monoethyl Ether (DEGEE) by the Scientific Committee on Consumer Products adopted Dec. 19, 2006 and copyrighted 2007 by the European Commission, p. 1-27, accessed via http://ec.europa.eu/health/ph_risk/committees/04_sccp/docs/sccp_o_082.pdf on Jan. 30, 2012.
http://en.wikipedia.org/wiki/surfactant, accessed Jan. 30, 2012.
http://npic.orst.edu/mcapro/pyrethroidsparesthesia.pdf, accessed Jan. 30, 2012.
http://en.wikipedia.org/wiki/paresthesiad, accessed Jan. 30, 2012.

* cited by examiner

*Primary Examiner* — Kortney L Klinkel
(74) *Attorney, Agent, or Firm* — Polsinelli Shughart

(57) ABSTRACT

The present invention relates to a liquid pest control system that includes a synthetic pyrethroid as a pest control active ingredient and an agent selected from the group consisting of purified diethylene glycol monoethyl ether, tocopherol nicotinate and tocopherol succinate, and combinations thereof, to reduce or eliminate paresthesia of the synthetic pyrethroid. The system releases the synthetic pyrethroid efficiently and uniformly. The pest control system is less irritating to the animal's skin as compared to prior art systems, particularly to small breeds of dogs. The system is useful for making liquid spot-on treatments, sprays and the like.

11 Claims, No Drawings

LIQUID PEST CONTROL FORMULATION

This patent application is a divisional of U.S. Ser. No. 12/876,122, filed Sep. 4, 2010, which claims the benefit of U.S. Provisional Ser. No. 61/249,968, filed Oct. 8, 2009. Both applications are incorporated herein by reference in their entirety.

FIELD OF THE INVENTION

The present invention relates to a liquid pest control system that includes a synthetic pyrethroid as a pest control active ingredient and an agent to reduce or eliminate paresthesia of the synthetic pyrethroid. The system releases the synthetic pyrethroid efficiently and uniformly. The pest control system is less irritating to the animal's skin as compared to prior art systems, particularly to small breeds of dogs. The system is useful for making liquid spot-on treatments, sprays and the like.

BACKGROUND OF THE INVENTION

Many pest control active ingredients cause irritation (paresthesia) to warm-blooded animals (including humans). This irritation to the skin and/or eyes of warm-blooded animals hampers the use of these pest control active ingredients. This irritation factor occurs even when the pest control active ingredient is blended with polymers or in other formulations (such as granules, dusts, dips, liquids, emulsions, etc.) wherein the active ingredient is considerably diluted.

The synthetic pyrethroid class of insecticides is known to cause paresthesia when coming into contact with the skin, with differing degrees of paresthesia being caused by different synthetic pyrethroids. Generally, the higher the degree of paresthesia, the more active the pyrethroid is against various insects; and those having a cyano group in their molecular structure produce a greater degree of paresthesia. While paresthesia is a transitory phenomenon, higher degrees of paresthesia have been known to cause severe trauma to animals' skins when applied thereto and have required days for the pain to end and weeks for the skin to repair. Thus, it has prevented some of the most beneficial efficacious pyrethroids from being used on animals due to the unacceptable dermatological effects produced on the animal.

Efforts to prevent or reduce the paresthesia effect of pyrethroids have been attempted with some success. However, in marketing these technologies to the total spectrum of the dog population, it was discovered that there is a small percentage of the total dog population, specifically the smallest dog breeds, that is more susceptible to pyrethroid-induced paresthesia than the general population and that this paresthesia in this group of small dogs is unacceptable.

It would be desirable to have a synthetic pyrethroid-containing product that not only reduces but actually eliminates paresthesia, including in the small dog breeds, and to have a liquid synthetic pyrethroid-containing product that would be suitable for treatment of small animals.

SUMMARY OF THE INVENTION

The present invention is directed to a method and a composition for the controlled delivery of a pest control active agent or a mixture of active agents while reducing or eliminating the irritation of the pest control active agent to warm blooded mammals, including to the smaller dog breeds such as Chihuahua, Shih Tzu, Jack Russell and other small terriers, Papillion, Brussels Griffon, Japanese Chin, Praxsky Krysarik, and the like that are typically particularly susceptible to pyrethroid-induced paresthesia. More particularly, the pest control system of the invention comprises a synthetic pyrethroid as the pest control active agent and an agent that reduces or eliminates paresthesia (identified herein and in the appended claims as a "paresthesia-reducing agent") selected from the group consisting of purified diethylene glycol monoethyl ether, tocopherol nicotinate, tocopherol succinate, and combinations thereof.

The formulation of the invention may optionally include other ingredients as necessary or desired, depending on the particular synthetic pyrethroid chosen and the form and intended use of the final product. Such optional ingredients can include, but are not limited to, additional non-synthetic pyrethroid pesticidal active agents; system carriers such as water, solvents, and the like; synergists; fragrances; coloring agents; preservatives; antioxidants; light stabilizers; and the like. Examples of the resulting liquid pest control system include, but are not limited to, a dip, a spray, or a spot-on.

The present invention is further directed to a method for reducing or eliminating the irritation to warm-blooded animals, and especially to the small breeds of dogs, of a liquid synthetic pyrethroid in a liquid pest control system, the method comprising associating a paresthesia-reducing agent (selected from the group consisting of purified diethylene glycol monoethyl ether, tocopherol nicotinate, tocopherol succinate, and combinations thereof) together with the synthetic pyrethroid in a pest control formulation, the amount of the paresthesia-reducing agent(s) present being an amount effective to reduce or eliminate the irritation of the synthetic pyrethroid to warm blooded animals. Such amount can be determined by one of ordinary skill in the art following the teachings herein without undue experimentation.

The system of the invention provides a non paresthesia-producing stable formulation that may, in one embodiment, include a high percentage of the irritating synthetic pyrethroid. This invention further allows for a high concentration of synthetic pyrethroid in a stable liquid formulation at room temperature, while reducing or eliminating any irritation of the synthetic pyrethroid. The formulation of the invention is effective without loss of the biological activity of the synthetic pyrethroid. This invention is particularly useful for reducing or eliminating the irritation of synthetic pyrethroids to the small dog breeds that are susceptible to pyrethroid-induced paresthesia.

DETAILED DESCRIPTION OF THE INVENTION

As used herein, "a" and "an" mean one or more, unless otherwise indicated.

"Paresthesia" as used herein and in the appended claims is defined as primarily a condition that results in a feeling (burning, tingling, and/or pricking sensation) of the skin.

To "eliminate the paresthesia," as used herein and in the appended claims, means that a formulation has a Paresthesia Rating of less than 1 for up to at least 24 hours in the Human Ear Assay, as described in the Examples hereinbelow.

As used herein, a "paresthesia-reducing agent" is an agent that reduces or eliminates paresthesia, particularly in the small breeds of dogs, and is selected from the group consisting of purified diethylene glycol monoethyl ether, tocopherol nicotinate and tocopherol succinate, and combinations thereof.

The pest control active agent may be chosen from any active agent known to cause paresthesia in warm-blooded animals, such as, but not limited to a synthetic pyrethroid. While the invention is particularly useful for delivering liquid synthetic pyrethroids at high concentrations in the formulation, the invention is not limited thereto but may also be used with synthetic pyrethroids at any concentration that results in the desired result of reducing or eliminating the paresthetic effects of the paresthesia-causing active agent while maintaining the active agent's pesticidal effects. One or more pesticidally active agents may be included within the formulation of the present invention, which may include active agents other than synthetic pyrethroids and active agents that do not cause paresthesia, as long as at least one active agent in the formulation is a synthetic pyrethroid. Exemplary pesticides and repellents which are effective against horn flies, face flies, stable flies, house flies, mosquitoes, lice, ticks, and mites are pyrethrin, cypermethrin, decamethrin, cyhalothrin, flumethrin, cyfluthrin, fenvalerate, deltamethrin, fempropathrin, fluvalinate, flucythrinate, cyfluthrin, alphamethrin, tralomethrin, cycloprothrin, karate, cyphenothrin (Gokilaht™), or any synthetic pyrethroid with a cyano group in its molecular structure. In one embodiment, the pest control active agent is a synthetic pyrethroid having a cyano group in its molecular structure.

Many of these active agents are effective both as a pesticide and a repellent, and the activity of many is enhanced by the inclusion of a synergist. Suitable synergists are known to those of skill in the art or can be determined without undue experimentation, examples of which include but are not limited to piperonyl butoxide and N-octyl bicycloheptene dicarboximide.

The second component of the composition of the present invention is a paresthesia-reducing agent selected from the group consisting of purified diethylene glycol monoethyl ether (CTFA/INCI Name: ethoxydiglycol), tocopherol nicotinate and tocopherol succinate, and combinations thereof. In one embodiment, only one paresthesia-reducing agent is present in the formulation. In one embodiment, a combination of two of the paresthesia-reducing agents is present in the formulation. In one embodiment, all three of the paresthesia-reducing agents are present in the formulation.

The diethylene glycol monoethyl ether must meet the following specifications to be specified as "purified" for use in this invention:

| | |
|---|---|
| Density | 0.978-0.9980 |
| refractive Index at 20° C. | 1.4260-1.4280 |
| Water Content | 0.00-0.10 |
| Acid Value | 0.00-0.10 mg KOH/g |
| Peroxide Value | 0.00-8.00 mg KOH/g |
| Boiling Point | 195-210° C. |
| Oxide Ethylene Content | 0.00-1.00 ppm |
| Ether Monomethylique EG Content | 0-50 ppm |
| Ethylene Glycol Content | 0-620 ppm |
| Diethylene Glycol Content | 0.250 ppm |
| Apparented Substances Total | 0.00-0.20% |

This ether is compatible with high concentrations (that is, of up to about 30 wt % or more, or of up to about 50 wt % or more, or of up to about 90 wt % or more) of liquid synthetic pyrethroids.

The amount of total paresthesia-reducing agent(s) in the formulation relative to the amount of synthetic pyrethroid will be an amount effective to reduce or eliminate the irritation or paresthesia caused by the synthetic pyrethroid. The effective amount is easily determinable by routine experimentation following the teachings herein. Generally, the total amount of paresthesia-reducing agent(s) in the formulation should be at least equal to the amount of synthetic pyrethroid and, often, the amount of the paresthesia-reducing agent(s) in the formulation is double to many times the amount of synthetic pyrethroid in the formulation in order to reduce the irritation value of the active agent. Thus, the ratio of paresthesia-reducing agent(s) to synthetic pyrethroid in one embodiment can be from about 1:1 to about 99.9:0.1. In one embodiment, the ratio can be from about 1:1 to about 5:1. In one embodiment, the ratio can be from about 1:1 to about 2:1.

When both tocopherol nicotinate and tocopherol succinate are present in the formulation, the ratio of nicotinate to succinate is from about 1:1 to about 3:1.

To prepare pest control systems according to the invention, the synthetic pyrethroid pest control active agent and the ether component are mixed with other ingredients as necessary or desired, depending on the particular active agent chosen and the form and intended use of the final product. The resulting formulation is then processed into the desired pest control system.

For example, the one or more pest control agent(s) and one or more paresthesia-reducing agents are mixed together with a suitable organic solvent, an aqueous solvent, or mixtures thereof. The liquid carrier is chosen such that the active agent(s) together with any optional additional ingredients form a liquid final product.

The following examples illustrate the practice of the invention. Parts are given as percentages and temperature in degrees Fahrenheit unless otherwise noted. "RT" is room temperature.

EXAMPLES

Example 1

Manufacturing Procedure

Formulations A-LL (see, Table 1 below) were prepared as follows: All ingredients were weighed and added to a heatable vessel. The vessel was then heated to 140° F., and the ingredients were stirred until a homogenous mixture was achieved. The mixture was then cooled to RT.

TABLE 1

| | Ingredients (wt %) | | | | | |
|---|---|---|---|---|---|---|
| Formulation | Gokilaht ™* | Nylar ®** | Solvent^ | Transcutol CG† | Tocopherol Nicotinate# | Tocopherol Succinate# |
| A | 42.5 | 2.1 | — | 55.4 | — | — |
| B | 32.5 | 2.1 | — | 65.4 | — | — |
| C | 22.5 | 2.1 | — | 75.4 | — | — |
| D | 12.5 | 2.1 | — | 85.4 | — | — |
| E | 2.5 | 2.1 | — | 95.4 | — | — |
| F | 1.0 | 2.1 | — | 96.9 | — | — |

TABLE 1-continued

| Formulation | Gokilaht™* | Nylar®** | Solvent^ | Transcutol CG† | Tocopherol Nicotinate# | Tocopherol Succinate# |
|---|---|---|---|---|---|---|
| G | 42.5 | 2.1 | — | 12.9 | 42.4 | — |
| H | 32.5 | 2.1 | — | 33.0 | 32.4 | — |
| I | 22.5 | 2.1 | — | 53.0 | 22.4 | — |
| J | 12.5 | 2.1 | — | 73.0 | 12.4 | — |
| K | 2.5 | 2.1 | — | 90.4 | 5.0 | — |
| L | 1.0 | 2.1 | — | 95.0 | 1.0 | — |
| M | 42.5 | 2.1 | — | 25.4 | — | 30.0 |
| N | 22.5 | 2.1 | — | 60.4 | — | 15.0 |
| O | 2.5 | 2.1 | — | 92.9 | — | 2.5 |
| P | 1.0 | 2.1 | — | 96.19 | — | 0.71 |
| Q | 42.5 | 2.1 | — | 14.6 | 30.4 | 10.4 |
| R | 32.5 | 2.1 | — | 34.5 | 23.2 | 7.7 |
| S | 22.5 | 2.1 | — | 54.0 | 16.0 | 5.4 |
| T | 12.5 | 2.1 | — | 73.5 | 8.9 | 3.0 |
| U | 2.5 | 2.1 | — | 93.0 | 1.8 | 0.6 |
| V | 1.0 | 2.1 | — | 95.9 | 0.75 | 0.25 |
| W | 42.5 | 2.1 | 12.9 | — | 42.4 | — |
| X | 32.5 | 2.1 | 33.0 | — | 32.4 | — |
| Y | 22.5 | 2.1 | 53.0 | — | 22.4 | — |
| Z | 12.5 | 2.1 | 73.0 | — | 12.4 | — |
| AA | 2.5 | 2.1 | 90.4 | — | 5.0 | — |
| BB | 1.0 | 2.1 | 95.0 | — | 1.0 | — |
| CC | 42.5 | 2.1 | 25.4 | — | — | 30.0 |
| DD | 22.5 | 2.1 | 60.4 | — | — | 15.0 |
| EE | 2.5 | 2.1 | 92.9 | — | — | 2.5 |
| FF | 1.0 | 2.1 | 96.19 | — | — | 0.71 |
| GG | 42.5 | 2.1 | 14.6 | — | 30.4 | 10.4 |
| HH | 32.5 | 2.1 | 34.5 | — | 23.2 | 7.7 |
| II | 22.5 | 2.1 | 54.0 | — | 16.0 | 5.4 |
| JJ | 12.5 | 2.1 | 73.5 | — | 8.9 | 3.0 |
| KK | 2.5 | 2.1 | 93.0 | — | 1.8 | 0.6 |
| LL | 1.0 | 2.1 | 95.9 | — | 0.75 | 0.25 |

*Gokilaht™ Technical 94.5% (d-cyphenothrin; synthetic pyrethroid); available from MGK Company.
**Nylar® Technical 100% (insect growth regulator; comprises approx. 50 wt % pyriproxyfen and approx. 50 wt % corn oil); available from MGK Company.
^aliphatic solvent, such as Isopar M™ (available from Exxon Chemicals).
†Transcutol CG is purified diethylene glycol monoethyl ether; supplied by Gattefossé Corp.
Tocopherol Nicotinate and Tocopherol Succinate are available from Sigma-Aldrich Corporation.

Testing:

The human ear assay is capable of discriminating between the effects of various formulations. Rapid penetration of the active agent in the ear lobe as well as the presence of the inferior maxillary of the trigeminus nerve system of the ear lobe tend to increase the sensitivity of the assay. It has been determined that a total volume of 10 μL of a formulation with an active volume (%) adjusted to 4 μL of technical active and applied to a human ear lobe provides, over time, an acceptable method of rating the paresthesia of formulations.

For purposes of evaluation of the discovery of this invention and to assist in determining the useful ratios of active agent to the paresthesia-reducing agent, the following screening procedure was set up:

1. Formulations are selected for evaluation.
2. A 10 μL sample of formulation to be evaluated is pipetted onto the ear lobe and left physically undisturbed. The paresthetic effect of this sample is evaluated within a 24-hour period.
3. The "Paresthesia Rating" is taken at the following time intervals following application of the formulation: 15 min, 30 min, 45 min, 1 hour, and each hour thereafter to 24 hours.
4. Irritation or sensitivity values are assigned according to the following scale ("Paresthesia Rating"):
   0=no sensation
   1=slight sensation
   2=sensation/no discomfort
   3=noticeable sensation
   4=slight discomfort
   5=noticeable discomfort
   6=uncomfortable
   7=very uncomfortable
   8=moderate hurting
   9=hurting
   10=severe hurting Formulations A-V in Table 1 were screened following this procedure and were found to have a Paresthesia Rating ("PR") of less than 1 at any given period within 24 hours and 0 at 24 hours. Formulations W and GG were also tested and were found to have a Paresthesia Rating ("PR") of less than 1 at any given period within 24 hours and 0 at 24 hours.

Example 2

Formulation "G" was tested on three Shih Tzu puppies with family history of being susceptible to cyphenothrin-induced paresthesia. The animals were examined and found to be in good health and happy. The animals were treated with 1.5 mL of the formulation (1.45 gm/0.655 gm cyphenothrin (0.687 gm technical Gokilaht)). Treatment was made by applying the dose to the animal's back, from the back of the neck to the back shoulders. The puppies were visually observed for signs of irritation or any reactions to the application of the formulation. The three puppies showed no signs of paresthesia reactions at any time between 0 to 31 hours.

Example 3

Formulation "G" was tested on two adult (2-year-old) Chihuahuas following the procedure of Example 2. Neither dog showed any signs of paresthesia reactions at 0 to 31 hours.

What is claimed is:

1. A liquid pest control formulation consisting of a synthetic pyrethroid and optionally an additional pesticidally active agent that does not cause paraesthesia and is not a synthetic pyrethroid, together with a paresthesia-reducing agent, wherein the paresthesia-reducing agent is a combination of tocopherol succinate, tocopherol nicotinate, and purified diethylene glycol monoethyl ether, and wherein the paraesthesia-reducing agent is present in an amount effective to reduce or eliminate the paraesthesia caused by the synthetic pyrethroid to dogs.

2. A liquid pest control formulation according to claim 1 wherein the synthetic pyrethroid is present in an amount of from about 1 wt % to about 50 wt % and the paresthesia-reducing agent is present in an amount of from about 50 wt % to about 99 wt %.

3. A liquid pest control formulation according to claim 1, wherein the formulation is a spot-on formulation.

4. A liquid pest control formulation comprising cyphenothrin and a paresthesia-reducing agent, wherein the paresthesia-reducing agent is a combination of tocopherol succinate and purified diethylene glycol monoethyl ether, and wherein the paresthesia-reducing agent is present in an amount of from about 50 wt % to about 99 wt % to reduce or eliminate the paresthesia caused by the cyphenothrin to dogs.

5. A liquid pest control formulation consisting of cyphenothrin and a paresthesia-reducing agent, wherein the paresthesia-reducing agent is a combination of tocopherol succinate and purified diethylene glycol monoethyl ether, and wherein the paresthesia-reducing agent is present in an amount of from about 50 wt % to about 99 wt % to reduce or eliminate the paresthesia caused by the cyphenothrin to dogs.

6. A liquid pest control formulation of claim 5, wherein the cyphenothrin is present in an amount of from about 1 wt % to about 50 wt %.

7. A liquid pest control formulation consisting of cyphenothrin, an insect growth regulator, and a paresthesia-reducing agent, wherein the paresthesia-reducing agent is a combination of purified diethylene glycol monoethyl ether and tocopherol succinate, and wherein the paresthesia-reducing agent is present in an amount of from about 50 wt % to about 99 wt %.

8. A method for reducing or eliminating paresthesia caused by a synthetic pyrethroid to dogs, the method comprising treating a dog with the liquid pest control formulation of claim 1.

9. A method for reducing or eliminating paresthesia caused by a synthetic pyrethroid to dogs, the method comprising treating a dog with the liquid pest control formulation of claim 4.

10. A method for reducing or eliminating paresthesia caused by a synthetic pyrethroid to dogs, the method comprising treating a dog with the liquid pest control formulation of claim 5.

11. A method according to claim 10 wherein the dog is a small breed.

\* \* \* \* \*